United States Patent [19]

Smiley

[11] 4,208,329

[45] Jun. 17, 1980

[54] OXAZOLE REMOVED FROM ACRYLONITRILE AS OXAZOLE SULFATE

[75] Inventor: Robert A. Smiley, Wilmington, Del.

[73] Assignee: E. I. Du Pont de Nemours & Co., Wilmington, Del.

[21] Appl. No.: 929,774

[22] Filed: Jul. 31, 1978

[51] Int. Cl.$^2$ .................. C07C 120/14; C07D 263/08
[52] U.S. Cl. ................. 548/239; 260/465.3; 260/465.9
[58] Field of Search ............. 260/465.3, 465.9, 307 R

[56] References Cited

U.S. PATENT DOCUMENTS

| | | | |
|---|---|---|---|
| 2,555,798 | 6/1951 | Kropa | 202/46 |
| 2,726,246 | 12/1955 | Trosken | 260/307 R |
| 2,895,959 | 7/1959 | Jeffreys et al. | 260/307 R |
| 3,185,636 | 5/1965 | Stevens et al. | 260/465.9 |
| 3,257,445 | 6/1966 | Roelen et al. | 260/465.3 |
| 3,468,624 | 9/1969 | Miller et al. | 260/465.9 |
| 3,522,268 | 7/1970 | Hall et al. | 260/307 R |
| 3,524,875 | 8/1970 | Hadley et al. | 260/465.3 |
| 3,574,687 | 4/1971 | Darcas et al. | 260/307 R |
| 3,600,424 | 8/1971 | Laviron et al. | 260/465.3 |
| 3,686,263 | 8/1972 | Maute | 260/465.3 |
| 3,697,576 | 10/1972 | Allirot et al. | 260/465.9 X |
| 3,989,705 | 11/1976 | Werstiuk | 260/307 R |

FOREIGN PATENT DOCUMENTS

| | | | |
|---|---|---|---|
| 1618144 | 1/1973 | Fed. Rep. of Germany | 260/465.9 |
| 1539255 | 10/1968 | France | 260/307 R |
| 44-27968 | 11/1967 | Japan | 260/307 R |
| 44-22091 | 9/1969 | Japan | 260/465.9 |
| 722543 | 1/1955 | United Kingdom | 260/307 R |
| 1130846 | 10/1968 | United Kingdom | |
| 1131134 | 10/1968 | United Kingdom | 260/307 R |
| 1156713 | 7/1969 | United Kingdom | 260/307 R |
| 1180556 | 2/1970 | United Kingdom | |

OTHER PUBLICATIONS

Abstract of Japan 74/11,272 of Mar. 15, 1974.
Cornforth, et al., J. Chem. Soc. (1947), pp. 96–102.
Wiley, Chem. Reviews, (1946), pp. 401–442.
Brown, et al., J. Chem. Soc. (1969), pp. 270–276.

*Primary Examiner*—Joseph Paul Brust
*Attorney, Agent, or Firm*—James A. Costello

[57] ABSTRACT

Oxazole is removed from acrylonitrile monomer by contacting the oxazole-containing acrylonitrile with sulfuric acid, forming the novel sulfate salt of the oxazole, separating the oxazole sulfate from the acrylonitrile and, if desired, the oxazole from the oxazole sulfate.

3 Claims, No Drawings

OXAZOLE REMOVED FROM ACRYLONITRILE AS OXAZOLE SULFATE

BACKGROUND OF THE INVENTION

1. Field of the Invention

This invention concerns the removal of color-forming oxazole from acrylonitrile monomer as oxazole sulfate from which oxazole can be readily recovered.

2. Description of the Prior Art

According to the so-called ammoxidation process for making acrylonitrile, propylene is reacted with ammonia and oxygen in the presence of a catalyst at about 450° C. There are several by-products of that reaction including oxazole. Oxazole, having the formula,

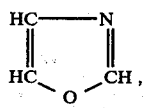

is a known compound. It is useful in insecticides against fiber-eating insects; see U.S. Pat. No. 3,359,158.

Oxazole has been characterized as a color-forming agent in the presence of acrylonitrile monomer. See, for example, U.S. Pat. No. 3,524,875, U.S. Pat. No. 3,686,263 and British Pat. No. 1,180,556.

Oxazole is removed from acrylonitrile according to U.S. Pat. No. 3,524,875 by a process of fractional distillation; according to U.S. Pat. No. 3,686,263 by complexing it with certain metal salts; according to British Pat. No. 1,180,556 by passing the oxazole-containing acrylonitrile through an ion exchange resin; and according to U.S. Pat. No. 3,697,576 by contacting it with an adsorbent (e.g., alumina, clay) for the oxazole.

According to the method of U.S. Pat. No. 2,555,798, acrylonitrile and a nonvolatile polybasic inorganic acid are treated by a steam distillation process. Certain unrelated salts of oxazole, including the picrate and the hydrochloride, are referred to in Cornforth et al. J. Chem. Soc. 96 (1947), pages 96 to 102. General background on oxazole is contained in Wiley, Chem. Rev. 37, (1945), pages 401 to 442. The Wiley article is concerned solely with substituted oxazoles.

SUMMARY OF THE INVENTION

This invention concerns a process for removing oxazole from acrylonitrile monomer in which minor amounts of water or other impurity may be present. It also concerns oxazole sulfate as a new composition of matter and the separation of oxazole therefrom.

The process for removing oxazole from a mixture comprising, among other things, oxazole and acrylonitrile comprises contacting the mixture with sulfuric acid, forming oxazole sulfate, and separating the oxazole sulfate from the acrylonitrile. Separation can be conducted by distillation, evaporation, filtration or decantation; or, by a combination of two or more such separation techniques; or, by any other technique(s) which will occur to those skilled in the art.

It has been found that the sulfuric acid must have a concentration of more than 70% or it will not react with the oxazole. So-called dilute sulfuric acids will not react with oxazole. In process embodiments such as distillation, dilute sulfuric acid is concentrated to a strength above 70% by virtue of water being taken off as an acrylonitrile-water azeotrope.

The oxazole sulfate reaction product of oxazole and sulfuric acid is a new composition of matter having the structure depicted in Example 14. Oxazole can be separated from the sulfate salt by hydrolysis and distillation with or without attendant basification to form a sulfate salt of the base. Oxazole forms an azeotrope with water, containing about 3% water (b.p. 68° C.) from which the water can be removed by using a desiccant or by other suitable means. Oxazole cannot be removed from acrylonitrile by extraction with water or dilute sulfuric acid.

In connection with the separation of oxazole sulfate from acrylonitrile by a distillation procedure which employs dilute sulfuric acid to begin with, it will be obvious that successive distillations can be employed with dilute or concentrated sulfuric acid until the acrylonitrile distillate has the desired low concentration of oxazole.

DETAILS OF THE INVENTION

It is preferred to employ a molar excess of sulfuric acid to oxazole when the process of separating acrylonitrile from the oxazole salt is accomplished, say, by distillation. The preferred molar ratio of sulfuric acid to oxazole is about 2:1 to 15:1. With an anhydrous mixture of acrylonitrile and oxazole, a stoichiometric amount of sulfuric acid to oxazole is preferred since excess sulfuric acid will increase the solubility of oxazole sulfate in the acrylonitrile.

Oxazole sulfate is a white crystalline solid having a melting point of 99° to 99.5° C. It is soluble in water where it hydrolyzes back to oxazole and sulfuric acid. In addition to the procedures described herein in detail for making and isolating oxazole sulfate, it can also be produced by neutralizing oxazole with concentrated sulfuric acid or oleum in an anhydrous medium in which oxazole sulfate is insoluble such as ketones and hydrocarbons.

The process for removing oxazole from acrylonitrile prepared by the ammoxidation reaction process can be accomplished in separation equipment installed just before the acrylonitrile is separated from high boiling by-products in the final stage of the process. For example, when the penultimate stage of the process concerns the drying of the acrylonitrile by azeotropic distillation, the separation process of this invention can be embodied in an evaporator installed between said drying stage and the final stage of acrylonitrile purification. The product from the drying stage can be fed into the evaporator to which sulfuric acid is also added. The oxazole sulfate which is formed is then taken off near the bottom of the evaporator and the oxazole-free or oxazole-lean acrylonitrile is sent to the product column in which acrylonitrile is separated from high boilers in the final stage of the ammoxidation process. Oxazole removal also may be accomplished by the addition of sulfuric acid directly to the final product column.

The storage stability and freedom from color of acrylonitrile is dependent on the amount of oxazole present in the monomer. The process of this invention can be used to remove oxazole to any desired level and the amount of oxazole in the final product can be monitored. Oxazole can be removed completely or small amounts of up to about 75 ppm can be allowed to remain in the acrylonitrile if it is determined that such amounts are acceptable in view of cost-to-remove versus the amount of color which can be tolerated in the acrylonitrile.

It is pointed out in connection with oxazole and color development that regardless of the amount of oxazole in the acrylonitrile exiting the final stage of the ammoxidation process, the acrylonitrile will be colorless. Color develops with time. The mechanism of color formation is not understood but it involves a reaction of oxazole with acrylonitrile.

The reaction product of oxazole and acrylonitrile has been found useful for dyeing nylon, silk and wool as well as other natural and synthetic substrates. On nylon, the oxazole-acrylonitrile dye has been found to fluoresce under ultraviolet light.

The unit of measure relied upon to express color herein is the APHA unit. APHA stands for American Public Health Association and the determination of APHA units was made in accordance with the text: "Standard Methods for the Examination of Water, Sewage and Industrial Wastes", 11th Ed., American Public Health Assn., New York (1955).

More specifically, the procedure employed to determine APHA color was as follows.

The liquid sample was placed in a one centimeter cell in a Carey spectrophotometer; distilled water was placed in a one centimeter cell in the second beam and the instrument was set in the visible light mode. A zero absorbance adjustment was made at 600 nm wavelength. A continuous absorbance record was then obtained by running the spectrophotometer from 600 nm down to 300 nm at a rate of 50 nm per minute. The absorbance at 380 nm was then read from the recorder chart and converted to APHA color by the formula:

$$APHA = \text{absorbance at 380 nm} \times 568$$

The 568 is a factor which correlates the 380 absorbance in a 1 cm cell to larger cell lengths and the original APHA color standards.

An APHA color $<15$ is colorless to the human eye while higher values are different shades of yellow, the higher the number the greater the degree of yellowness. On a scale of 0 to 500 the degree of color is: colorless, very light yellow, light yellow, yellow, dark yellow, and very dark yellow.

EXAMPLES

The following Examples illustrate the invention.

EXAMPLES 1 to 9 AND COMPARISONS A TO D

A simple distillation apparatus consisting of a 200 ml round-bottom flask and distillation head with attached condenser was set up. A series of identical distillations were run in it starting each distillation with 100 ml of dry acrylonitrile containing 640 ppm (0.064%) of oxazole to which various acids and different concentrations and amounts of sulfuric acid was added prior to distillation. Exactly 75 ml of distillate was collected during each distillation (at atmospheric pressure) and the oxazole concentration in the distillate determined by gas-phase chromatography (10'×⅛" column packed with "Chromosorb" 104, isothermal determination at 160° C., Hewlett-Packard Model 5730A, flame ionization detector). The results were:

100 ml of ACRN = 80 gm (1.51 moles)
0.064% × 80 = 0.0512 gm of oxazole (0.00074 moles)

TABLE

| Ex. No., Control, Or Comparison Letter | Acid Added | Amt. Mole g (moles) | Mole Acidyl Distillate Oxazole | Oxazole in (ppm) |
|---|---|---|---|---|
| Control | none | — | — | 640 |
| 1 | 120% $H_2SO_4$ | 0.35 (0.004) | 5.4 | 140 |
| 2 | 96% $H_2SO_4$ | 0.42 (0.004) | 5.4 | 30 |
| 3 | 96% $H_2SO_4$ | 0.63 (0.006) | 8.1 | 10 |
| 4 | 96% $H_2SO_4$ | 0.21 (0.002) | 2.7 | 200 |
| 5 | 96% $H_2SO_4$ | 0.15 (0.0015) | 2.0 | 320 |
| 6 | 50% $H_2SO_4$ | 0.84 (0.004) | 5.4 | 60 |
| 7 | 40% $H_2SO_4$ | 1.05 (0.004) | 5.4 | 90 |
| 8 | 20% $H_2SO_4$ | 2.1 (0.004) | 5.4 | 100 |
| 9 | 10% $H_2SO_4$ | 4.2 (0.004) | 5.4 | 150 |
| A | 85% $H_2SO_4$ | .49 (0.004) | 5.4 | 460 |
| B | Benzene sulfonic | .68 (0.004) | 5.4 | No distillate[1] |
| C | Toluene sulfonic | .74 (0.004) | 5.4 | No distillate[1] |
| D | Methane sulfonic | .41 (0.004) | 5.4 | No distillate[1] |

[1] There was rapid polymerization and no distillate formed.

The data show that sulfuric acid is useful in removing oxazole whereas phosphoric acid is relatively ineffective and the other sulfonic acids cause a solid-reducing reaction. Sulfuric acid as weak as 10% can be employed in the distillation process but is not as effective as more concentrated sulfuric acid. The greater the molar excess of sulfuric acid to oxazole, the more effective the removal of oxazole becomes. A molar ratio of 2 resulted in removal of less than half of the starting oxazole, while a ratio of 8 resulted in an oxazole reduction of over 98%. Nearly complete oxazole removal can be achieved at $H_2SO_4$/oxazole ratios of about 8 or more.

Usefulness of $H_2SO_4$ at the concentrations set out in the Table is attributable to the increase in concentration, to above 70%, which takes place during distillation. See Example 15, hereafter, which demonstrates that oxazole sulfate is not formed unless the concentration of $H_2SO_4$ is in excess of 70%.

EXAMPLE 10

A substantially dry sample of acrylonitrile taken from a plant distillation tower was analyzed by gas chromatography and found to contain 720 ppm of oxazole.

A 50 g (0.9423 mole) aliquot of the sample containing 0.036 g (0.00052 mole) of oxazole was charged to a still together with 0.50 g of 96% sulfuric acid (containing 0.48 g of sulfuric acid on a water-free basis; 0.00488 mole) and flash distilled at atmospheric pressure until 50 ml of distillate boiling at 77° C. was collected. The sulfuric acid/oxazole mole ratio was 9.4 on a water-free basis. The distillate was analyzed and found to contain about 10 ppm of oxazole.

EXAMPLE 11

By the procedure of Example 10, an aliquot containing 0.25 g of 96% sulfuric acid (0.00244 mole) was flash distilled at a mole ratio of 4.6 sulfuric acid to oxazole. The distillate contained 90 ppm of oxazole.

To remove additional oxazole from the distillate, the distillate could have been redistilled with additional sulfuric acid one or more times until the desired low oxazole level was achieved. In each redistillation, the sulfuric acid concentration and the molar proportions of sulfuric acid to oxazole could have been varied as described herein.

EXAMPLE 12

By the procedure of Example 10, an aliquot containing 0.786 g of 96% sulfuric acid (0.00770 mole) was flash distilled at a mole ratio of 14.8 sulfuric acid to oxazole. The distillate contained no detectable oxazole.

EXAMPLE 13

A sample of commercial acrylonitrile monomer was analyzed by gas chromatography and found to contain 370 ppm of oxazole.

A 200 g (3.77 mole) aliquot of the sample containing 0.074 g (0.00107 mole) of oxazole was charged to a still together with 0.4 g of 96% sulfuric acid (containing 0.384 g, 0.0039 mole of sulfuric acid on a water-free basis) and distilled at 200 mm Hg through a 5-plate Oldershaw column. Distillate boiling at 38°–39° C. was collected. The sulfuric acid/oxazole mole ratio was 3.65. The distillate was analyzed and contained 0.07% water and no detectable oxazole.

EXAMPLE 14

An amount, 9.8 gm (0.1 mole) of 100% sulfuric acid, was added to a solution of 6.9 gm (0.1 mole) of pure oxazole in 200 ml of anhydrous acrylonitrile. The solid which formed was filtered off on a suction filter, slurried in 200 ml of acetone and refiltered. The cake was dried under vacuum for five hours. The dry oxazole sulfate melted sharply at 99°–99.5° C. The solid dissolved readily in water which when analyzed by G.C. showed the presence of oxazole. An N.M.R. spectrum of oxazole sulfate in deuterated dimethylsulfoxide showed three oxazole protons and the two protons of sulfuric acid. Thus, the structure of oxazole sulfate can be written as:

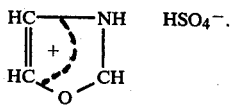

EXAMPLE 15

This Example describes the determination that sulfuric acid must have a concentration in excess of 70% to react with oxazole.

Diphenylamine and oxazole have the same base strengths. Concerning oxazole ($pK_a$ 0.8), see J. Chem. Soc. (8) 1969, page 273 and concerning diphenylamine ($pK_a$ 0.79), see The Chemist's Companion, Gordon et al, Wiley (1972) page 59. Thus, substantially the same strength acid which reacts with diphenylamine to form the diphenylamine salt will react with oxazole to form the oxazole salt.

One gram of diphenylamine was added to 10 g of sulfuric acid of various strengths in small bottles. Each bottle was vigorously shaken to thoroughly mix the solid amine with the acid. The results were:
96% $H_2SO_4$—solution
90% $H_2SO_4$—solution
80% $H_2SO_4$—solution
70% $H_2SO_4$—the diphenylamine remained insoluble
60% $H_2SO_4$—the diphenylamine remained insoluble
50% $H_2SO_4$—the diphenylamine remained insoluble
40% $H_2SO_4$—the diphenylamine remained insoluble Thus, sulfuric acid in excess of 70% concentration is required to dissolve diphenylamine, presumably by forming diphenylamine sulfate. The 70% $H_2SO_4$ slurry was diluted to 100 g with additional 70% $H_2SO_4$ but the solid remained undissolved, showing that the amine salt had not formed. Had the amine salt formed it would have dissolved when the additional 70% $H_2SO_4$ was added. Since oxazole and diphenylamine have the same $pK_a$, it can be concluded that oxazole will not form a salt with 70% sulfuric acid.

EXAMPLE 16

Acrylonitrile containing 0.42% of oxazole was dried by azeotropic distillation in a 40 gal capacity, 10 plate packed still. One gallon cuts of heart-cut distillate were taken and analyzed for oxazole. All cuts containing 0.6% or more of oxazole (max. about 3%) were placed in 1 gallon glass bottles. Commercial grade 96% $H_2SO_4$ was added to each bottle to neutralize the oxazole. After standing overnight, the precipitated oxazole sulfate was filtered off from each gallon, combined and dried of acrylonitrile in a vacuum oven.

In an isolation sequence, 449 g of oxazole sulfate was slurried in 200 ml of distilled water and 300 ml of concentrated $NH_4OH$ was added dropwise with stirring and cooling. After the neutralization, the oxazole was distilled out through a 40 plate, 1 inch Oldershaw column at atmospheric pressure; and 152 g of constant boiling oxazole distillate was collected, a recovery of 82%. The boiling point of the oxazole was 68° C. Analysis showed the presence of about 3% of water in the product oxazole which was removed by drying over a 4 A molecular sieve. The refractive index of oxazole ($n_D^{25}$) is 1.4248.

EXAMPLE 17

About 20 ml of acrylonitrile containing 390 ppm of oxazole was poured into a beaker and a drop of 96% $H_2SO_4$ was added. A cloudy precipitate formed but no heat was evolved nor was there any evidence of acrylonitrile polymerization. A G.C. analysis after filtration (to give a clear filtrate) showed only 30 ppm of oxazole left. Another drop of acid was added without any visible effect. Analysis by G.C. indicated about 20 ppm of oxazole.

About 10 drops of 96% $H_2SO_4$ was then added to 50 ml of the same anhydrous acrylonitrile containing 390 ppm of oxazole. No color change occurred and there was no heat evolution; a small amount of white fluffy precipitate formed. This material was distilled at atmospheric pressure until about 10 ml of distillate was collected. No color change in the pot occurred, the residue remaining water clear. G.C. analysis showed no oxazole in the distillate.

EXAMPLE 18

Oxazole sulfate was isolated as a solid by the addition of 96% $H_2SO_4$ to dry (0.07% $H_2O$) acrylonitrile containing 0.22% of oxazole. The oxazole sulfate separated as a white crystalline solid which was readily filtered off and dried.

EXAMPLE 19

An accelerated color stability test, at 43° C., was run on acrylonitrile containing various amounts of oxazole, said acrylonitrile containing 40 ppm of polymerization inhibitor. The results were as follows:

| Oxazole, PPM | APHA Color After | | |
|---|---|---|---|
| | 1 Mo. | 2 Mo. | 3 Mo. |
| 200 | 216 | 449 | 471 |
| 100 | 34 | 230 | 392 |
| 50 | 12 | 85 | 128 |
| 25 | 4 | 18 | 37 |
| 12.5 | 0 | 4 | polymerized |

This test shows in a general way the relationship between the amount of oxazole and the amount and speed of color formation. Polymerization of the 3 month low oxazole sample may indicate easier polymerizability of acrylonitrile containing such low levels of oxazole compared to acrylonitrile containing higher oxazole levels. If desired, higher levels of polymerization inhibitor can be employed to retard polymerization of ACRN containing such low oxazole levels.

The embodiments of the invention in which an exclusive property or privilege is claimed are defined as follows:

1. In a process for removing oxazole from a mixture comprising acrylonitrile and oxazole prepared by the ammoxidation of propylene, the improvement which comprises contacting the mixture with sulfuric acid having a concentration greater than 70% forming oxazole sulfate of the formula:

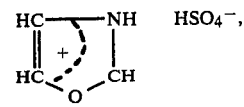

and separating the oxazole sulfate from the acrylonitrile.

2. The composition of matter, oxazole sulfate, having a melting point of 99° to 99.5° C. and the formula:

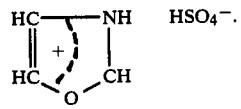

3. A process for making oxazole sulfate, with a melting point of 99° to 99.5° C. and the formula:

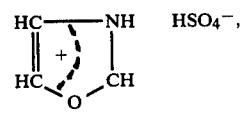

comprising contacting oxazole with sulfuric acid having a concentration greater than 70%.

* * * * *